United States Patent [19]

Kathawala et al.

[11] 4,384,124

[45] May 17, 1983

[54] CYCLOPROPANYL-BEARING AMIDES OF TRYPTOPHANE

[75] Inventors: Faizulla G. Kathawala, West Orange, N.J.; John G. Heider, West Nyack, N.Y.

[73] Assignee: Sandoz, Inc., E. Hanover, N.J.

[21] Appl. No.: 168,194

[22] Filed: Jul. 10, 1980

Related U.S. Application Data

[60] Division of Ser. No. 9,473, Feb. 5, 1979, Pat. No. 4,248,893, which is a continuation-in-part of Ser. No. 872,836, Jan. 27, 1978, abandoned.

[51] Int. Cl.³ .................... C07D 209/20; A61K 31/41
[52] U.S. Cl. .................................. 548/495; 424/274
[58] Field of Search ............................... 260/326.14 T

*Primary Examiner*—Donald G. Daus
*Assistant Examiner*—D. B. Springer
*Attorney, Agent, or Firm*—Gerald D. Sharkin; Richard E. Vila; Frederick H. Weinfeldt

[57] ABSTRACT

Cyclopropanyl-group-bearing-amides, eg N-[1-(benzyl)-2-(phenyl)ethyl]-cis-2-octyl-cyclopropanoctanamide and N-(α-methyl-benzyl)-(cis)-2-octyl-cyclopropanoctanamide, are useful as pharmaceutical agents and are obtainable, eg by reacting a mixed anhydride of a cyclopropanyl-group bearing-long chain carboxylic acid with an appropriate amino compound.

11 Claims, No Drawings

CYCLOPROPANYL-BEARING AMIDES OF TRYPTOPHANE

This is a division of application Ser. No. 9,473 filed Feb. 5, 1979 now U.S. Pat. No. 4,248,893 (issued Feb. 3, 1981) which in turn is a continuation-in-part of Ser. No. 872,836, filed Jan. 27, 1978, now abandoned.

This invention relates to organic compounds and more particularly to cyclopropanyl-group bearing-amides and to pharmaceutical compositions containing such compounds, as well as to the pharmaceutical use of such compounds.

The compounds of this invention are conveniently represented by the formula I:

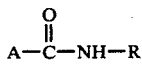

wherein
A is an unsaturated fatty acid hydrocarbon chain of 7 to 23 carbon atoms in which each unsaturated ethylene moiety, i.e. of the formula:

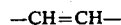

is replaced by a cyclopropanyl group of the formula

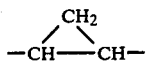

said A having 1 to 4 such cyclopropanyl groups; and R is:

(a) an aralkyl radical of the structure

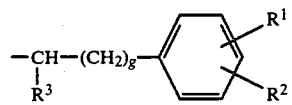

wherein
g is 0 or 1;
wherein
$R^1$ is a hydrogen atom, halo having an atomic weight of from about 19 to 80, ie. fluoro, chloro or bromo, alkoxy having from 1 to 3 carbon atoms, eg methoxy; or alkyl having from 1 to 3 carbon atoms, eg methyl;
$R^2$ is a hydrogen atom, alkyl having from 1 to 3 carbon atoms, alkoxy having from 1 to 3 carbon atoms, or halo having an atomic weight of from about 19 to 36, ie fluoro or chloro; and
$R^3$ is
(i) a hydrogen atom, a phenyl radical of the structure (ii)
(ii)

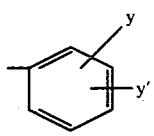

wherein
y is a hydrogen atom, halo having an atomic weight of from about 19 to 80, ie. fluoro, chloro or bromo, alkoxy having from 1 to 3 carbon atoms, eg methoxy; or alkyl having from 1 to 3 carbon atoms, eg methyl; and
y' is a hydrogen atom, alkoxy having from 1 to 3 carbon atoms, alkyl having from 1 to 3 carbon atoms, or halo having an atomic weight of from about 19 to 36, ie fluoro or chloro; or a benzyl radical of the formula (iii)
(iii)

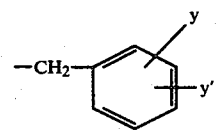

wherein y and y' are as defined above; or
(iv) alkyl having from 1 to 8 carbon atoms; or R is:
(b) a phenyl radical of the structure

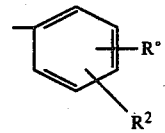

wherein
$R^2$ is as defined above, and
$R°$ is a hydrogen atom, halo having an atomic weight of from about 19 to 80, ie fluoro, chloro or bromo, alkyl having from 1 to 3 carbon atoms; alkoxy having from 1 to 3 carbon atoms; or a radical of the structure $R^f$:

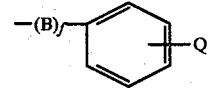

in which
B is $-CH_2-$ or $-O-$;
f is 0 or 1; and
Q is a hydrogen atom, halo having an atomic weight of from about 19 to 80, alkoxy having from 1 to 3 carbon atoms, or alkyl having from 1 to 3 carbon atoms;
or R is:
(c) a tryptophanyl radical of the structure:

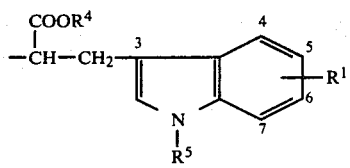

wherein
$R^1$ is as defined above, and
$R^4$ is alkyl having from 1 to 8 carbon atoms, or benzyl (unsubstituted); and
$R^5$ is a hydrogen atom, alkyl having from 1 to 8 carbon atoms or benzyl (unsubstituted);
or R is
(d) a benzocycloalkyl nucleus of the structure:

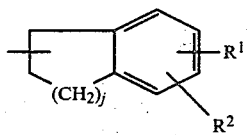

wherein
$R^1$ and $R^2$ are as defined above; and
j is a whole integer of from 1 to 4.

Compounds I may be obtained by acylation (process a) of an amine of formula II:

$$H_2N-R \qquad II$$

in which R, is as defined above, with a cyclopropanyl-bearing-fatty acid or derivative thereof corresponding to the moiety -A as defined above. Such "acylation" may be carried out by means conventionally employed in converting an amine function to its corresponding amide, such as are reported in the literature.

The acylation (process a) may conveniently be carried out by a mixed anhydride technique (process a1) wherein a compound II is treated with a mixed anhydride of the formula III:

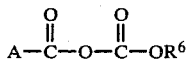
$$\text{III}$$

in which A is as defined above and $R^6$ is a lower unbranched alkyl having from 1 to 6 carbon atoms, at moderate temperatures, eg from about $-10°$ C. to $+35°$ C., in an inert organic medium, eg a chlorinated hydrocarbon, such as methylene chloride.

The mixed anhydrides (III) are obtainable by reacting (process b1) a free carboxylic acid of the formula IV:

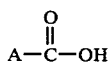
$$\text{IV}$$

wherein A is as defined above, with a chloroformate of the formula V,

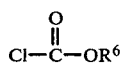
$$\text{V}$$

wherein $R^6$ is as defined above, in the presence of an acid acceptor, eg an organic base, such as triethylamine, at reduced temperatures, eg at from about $-10°$ to $+30°$ C., in an inert organic medium, eg a chlorinated hydrocarbon, such as methylene chloride.

Another convenient method of preparing compounds I comprises reacting (process a2) an acyl halide of the formula VI

$$\text{VI}$$

in which A is as defined above, and X is either chloro or bromo, with a compound II (as defined above), in the presence of an acid acceptor, in an inert medium at moderate temperatures, eg from about 10° to 50° C. preferably at about 20° to 30° C.

The acyl halides (VI) may be prepared in the conventional manner, eg by treating (process b2) a corresponding compound IV (as defined above), with a halogenating agent capable of contributing a chlorine or bromine atom, eg thionyl chloride (or -bromide, as appropriate).

In the above-described processes, neither the media nor the temperature are critical to the reactions, and where the reactants or reagents are liquid, an excess thereof may serve as the reaction medium. If desired a compound II may be in the form of a water-soluble acid addition salt, for example the hydrochloride. The mixed anhydride (III) (resulting from process b1) may conveniently be used in situ. That is to say that provided that the materials in the reaction mixture containing the mixed anhydride are not detrimental, they may be used (directly for process a1) without recovery.

Reagents and reactants described herein, e.g., compounds II, III, IV, V, and VI are known and obtainable by known means, or where not known, may be obtained by adaptation of methods reported in the literature for the preparation of known analogs; many such compounds being commercially available.

With respect to R, when it is of type (a) or (b) and $R^o$ is not $R^f$, it is preferred that when $R^1$, $R^o$ or y is other than a hydrogen atom and $R^2$ (or y') is a hydrogen atom, that $R^o$, or $R^1$, or y be located at the 2-position; and that when $R^2$ (or y') is also other than a hydrogen atom that $R^1$ or $R^o$ and $R^2$ (or y and y') are the same, and it is additionally preferred that they be located at the 2- and 6-positions of the phenyl ring. When R is of type (a) where g=1, and $R^3$ is of type (ii), then R can be an α-(phenyl)-β-(p-methylphenyl)ethyl radical, and when $R^3$ is of type (iii), then R can be an α-(benzyl)-phenylethyl radical.

With particular respect to the substituent $R^o$ when it is a radical $R^f$, it will be appreciated that when $B=CH_2$ and $f=1$, then the radical $R^f$ is of the benzyl type. When B=oxygen and f=1, then the radical $R^f$ is of the phenoxy-type. When f=zero, then the radical $R^f$ is of the phenyl-type. Hence, when R is of type (b) and $R^o$ is of type $R^f$ where f=zero, then R can be a biphenylyl radical. The radical $R^f$ is preferably at the para-position. When Q is other than a hydrogen atom, it is preferably at the para-position.

With respect to R, when it is of type (c), it is preferred that when $R^1$ is other than a hydrogen atom, it be located at the 5-position of the indole nucleus. It is also preferred that when $R^4$ is alkyl, it is unbranched, particularly ethyl.

With respect to R when it is of type (d) it is preferred that when $R^1$ is other than a hydrogen atom, that it be located at a carbon atom ortho to the ring junction; and that when $R^2$ is also other than a hydrogen, it is preferred that it be the same as $R^1$, and it is additionally preferred that it be in para-relationship to $R^1$. It is additionally preferred that the amide group be linked to a carbon of the cycloalkyl moiety which is directly bonded to a ring junction carbon. It is also preferred that j be 1, ie, that the benzocycloalkyl nucleus be indanyl, and particularly 1-indanyl.

In the above-presented definitions, when $R^o$, $R^1$ or y is halo, it is preferably fluoro or chloro, and particularly chloro; and when $R^2$ or y' is halo it is preferably chloro.

Cyclopropanyl group-bearing fatty acids (IV) are conveniently obtained by converting the ethylenically unsaturated positions of corresponding long chain unsaturated fatty acids to cyclopropanyl groups. It will be appreciated that each olefinic unit: —CH=CH— is thus replaced by a propanyl unit:

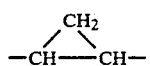

Since each cyclopropanyl unit contributes an additional carbon atom to the non-cyclic portion of the hydrocarbon radical A, the total number of carbon atoms in A will equal the number of carbon atoms in the non-cyclic portion plus the total number of cyclopropanyl units thereon.

For example, compounds suitable as cyclopropanyl-bearing acids (IV) (or their derivatives) are obtainable by treatment of a corresponding mono- or poly-unsaturated long chain fatty acid (VII) with methyleneiodide ($CH_2I_2$) by the Simmons-Smith method (described in J.A.C.S. 81, 4256 (1959).

For preparing compounds IV bearing a single cyclopropanyl unit, the starting acids (VII) may possess either the cis-oid or trans-oid configuration. When acids with cis-oid configuration are used, the Simmons-Smith reaction, used for preparing the corresponding "cyclopropane" acids (IV), leads only to cis "cyclopropane" acids, and similarly the trans-acids gives the corresponding trans-"cyclopropane" acids. Mixtures will of course lead to corresponding mixture. When a cyclopropane acid is reacted with an appropriate amine, R—NH (II), which carries any asymmetric carbon atoms, to give the amide (I), it will be appreciated that the resulting amide (I) is obtained as a mixture of diastereoisomers, which may be separated, through known recovery methods, such as chromatography and crystallization. Alternatively, if desired, the starting cyclopropane acid may be resolved into its antipodes, and a particular antipode then reacted with the desired optical isomer of an amine (II), to give the corresponding isomeric product in relatively pure isomeric form.

Similarly, for preparing cyclopropane acids (IV) bearing two or more cyclopropanyl units, the starting olefinic acids have a corresponding number of double bonds, and the Simmons-Smith reaction leads to a mixture of diastereomeric acids, which may be separated before reacting with the appropriate amine (II).

Since compounds I having only one cyclopropanyl unit have a lesser number of asymmetric carbon atoms than those derived from acid of greater unsaturation, they are generally easier to refine and are therefore, preferred from that standpoint, where ease of purification is an important factor in their preparation.

In general it is preferred that A is unbranched. It is further preferred that each pair of hydrogen atoms bound to the tertiary carbon atoms of each cyclopropanyl group is in the cis configuration.

A preferred class of Compounds I are those wherein A is a cyclopropanyl-bearing hydrocarbon radical of the formula A1:

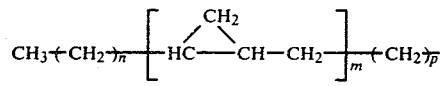

wherein n is a whole integer of from 1 to 15; m is 1 or 2; and p is a whole integer of from 1 to 13, provided that when m is 1, then n+p is from 3 to 19, and when m is 2 then n+p is from 2 to 16; and particularly those having in addition to the various preferences discussed above, one or more of the following characteristics with respect to the A-moiety: (1) n+p=7 to 19 when m is 1; or n+p=4 to 16 when m=2; (2) n+p=an odd number when m=1, and an even number when m=2; and (3) when m=1, then n=5 or 7 and p=6; and when m=2, then n=4 and p=6.

In view of the above-presented preferences it will be appreciated that it is particularly preferred that in compounds I the A-moiety is derived from mono- or diunsaturated fatty acids (or esters thereof) of the type found in nature, especially palmitoleic or oleic acid (m=1); and linoleic acid (m=2).

Particular embodiments of this invention are the compound N-(α-methylbenzyl)-2-octyl-cyclopropanoctanamide (cis isomer) of Example 1, and pharmaceutical compositions containing said compound, as well as the use of said compound and compositions containing said compound as described herein.

Additional particular embodiments of this invention are the compound N-[α-(p-methylbenzyl)-p-methylphenyl ethyl]-cis-2-octyl-cyclopropanoctamide of Example 4, and pharmaceutical compositions containing said compound, as well as the use of said compound and compositions containing said compound as described herein.

Additional particular embodiments of this invention are the compound N-[α-(benzyl)-β-(phenyl)ethyl]-cis-2-octyl-cyclopropanoctamide of Example 7, and pharmaceutical compositions containing said compound, as well as the use of said compound and compositions containing said compound as described herein.

STATEMENT OF UTILITY

The compounds of formula I of this invention are useful as pharmaceutical agents in animals. In particular, the compounds of the formula I are useful in controlling the cholesterol ester content of mammalian arterial walls and are therefore particularly indicated for use as antiatherosclerotic agents, ie. agents useful in the prophylactic treatment of atherosclerosis and in the controlling of atherosclerotic conditions due to cholesterol ester accumulation in the arterial walls. Such ability of the compounds of the formula I is indicated by known test procedures in which the total cholesterol ester content of cultured cells is shown to be reduced by a test compound, as compared to untreated cells, and carried out, for example, by the following procedures:

(A) Cell culture

Rhesus monkey smooth muscle cells (from the arterial, eg aorta, wall) obtained by the method of K. Fisher-Dzoga et al (Experimental and Molecular Pathology 18, 162–176 (1973)) are routinely grown in 75 $cm^2$ tissue culture flasks using Minimum Essential Medium (Eagle) supplemented with 10% fetal bovine serum. For testing a 75 $cm^2$ flask with a near confluent cell growth is selected. The cells are removed from the flask surface by mild enzymatic treatment with pronase. After centrifugation and decanting in enzyme solution, the cell pellet is resuspended in an appropriate volume of media for seeding the desired number of 60 mm tissue culture dishes. Five (5) ml of the diluted cell suspension are pipetted into each dish. After seeding, the dishes are labelled with the cell type, date and flask number of origin and incubated at 37° C. in approximately 5% $CO_2$ atmosphere in a high humidity incubator. When the cultures are confluent, the actual drug testing is begun. Test compounds are routinely solubilized in 100% ethanol. An equivalent amount of ethanol is added to control groups as well. The tissue culture dishes are randomly divided into groups. To one group, hyperlipemic rabbit serum (HRS) is added at 5% by volume (control). To the remaining groups, 5% HRS and 1 mg per 100 ml of media of the test compound are added. The dishes are returned to the incubator for an additional 24 hours. All operations through to the final incubation are performed using sterile technique in a laminar flow hood. After the incubation period, the dishes are microscopically observed with the Zeiss Axiomat with phase contrast optics and the conditions of the cultures are recorded; especially in regard to the size, number and configuration of cytoplasmic inclusions and to cellular morphology. The media is removed from the cultures and 0.9% sodium chloride solution is added. The cells are removed from the flasks with the aid of a rubber policeman and transferred to a conical graduated centrifuge tube. The cells are washed three times by suspending in an isotonic salt solution, centrifuging at 800×g for 10 minutes and aspirating the supernatant fluid.

(B) Cell extraction procedure

An appropriate volume of isopropyl alcohol (about 1 ml/mg protein) is then added to the cell pellet and the sample sonicated with a micro probe (140×3 mm) for 10 seconds with a "LO" setting of 50 on a Bronwell Biosonik IV. After centrifugation for 15 minutes at 800×g, the clear supernatant is decanted and an aliquot taken for cholesterol analysis.

The residue is dissolved in 0.1 N sodium hydroxide and an aliquot taken for protein determination by the method of Lowry, et al. (J. Biol. Chem. 193, 265; 1951).

(C) Assay

Free cholesterol: The isopropyl alcoholic solutions of standards, samples and blank (isopropyl alcohol alone) are treated in a similar manner. An aliquot of 0.4 ml of free reagent (Reagent A, Table 1 below) is added to a 10×75 mm disposable glass test tube to which 20 μl of the isopropyl alcoholic solution is added and mixed. After standing at room temperature for approximately 5 minutes, 0.8 ml of 0.5 N sodium hydroxide (Reagent C, Table 1) is added and mixed. The fluorescence is measured with an Aminco-Bowman spectrophotofluorometer with an excitation wavelength of 325 nm and emission wavelength of 415 nm. A 1 cm light path cuvette is used with a xenon lamp, an IP28 photomultiplier tube and 2 mm slits.

Total cholesterol: The same procedure described above for free cholesterol is followed for total cholesterol except that the total reagent (Reagent B, Table 1) is used instead of the free reagent and the samples are incubated for 20 minutes at 37° C. before the addition of the 0.5 N sodium hydroxide solution (Reagent C, Table 1).

Alternatively, the assay for cholesterol, ie Step C (above) obtained from Steps A and B, may be carried out by the method of Ishikawa et al (J. Lipid Res. 15, 286; 1974).

The amount of cholesterol ester is found by subtracting the amount of free cholesterol from the total cholesterol content of the cells determined by the assay. A finding of a lower amount of cholesterol ester in the group of cells to which test compound was added, as compared to the control group (untreated) shows that the test compound is active in reducing the cholesterol ester in the cells.

TABLE 1

Composition of Reagents for Cholesterol Determination

| | | | |
|---|---|---|---|
| A. | Free Cholesterol Reagent | | |
| | Sodium phosphate buffer pH 7.0 | .05 | M |
| | Cholesterol oxidase | .08 | U/ml |
| | Horseradish peroxidase | 30. | U/ml |
| | p-Hydroxyphenylacetic acid | .15 | mg/ml |
| B. | Total Cholesterol Reagent | | |
| | Sodium phosphate buffer pH 7.0 | .05 | M |
| | Cholesterol ester hydrolase | .08 | U/ml |
| | Cholesterol oxidase | .08 | U/ml |
| | Horseradish peroxidase | 30. | U/ml |
| | Sodium taurocholate | 5. | mM |
| | Carbowax-6000 | .17 | mM |
| | p-Hydroxyphenylacetic acid | .15 | mg/ml |
| C. | Sodium Hydroxide Solution | .5N | |

When the compounds are employed for the above utility, they may be combined with one or more pharmaceutically acceptable carriers, e.g., solvents, diluents and the like, and may be administered orally in such forms as tablets, capsules, dispersible powders, granules, suspensions containing, for example, from about 0.5 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.5 to 5% suspending agent in an isotonic medium. These pharmaceutical preparations may contain, for example, from about 0.5% up to about 90% of the active ingredient in combination with the carrier, more usually between 5% and 60% by weight.

The antiatherosclerotic effective dosage of active ingredient employed for the reduction of cholesterol ester content in the arterial walls of a mammal may vary depending on the particular compound employed, the mode of administration and the severity of the condition being treated. However, in general, satisfactory results are obtained when the compounds of formula I are administered at a daily dosage of from about 2 milligrams to about 500 milligrams per kilogram of animal body weight, preferably given in divided doses two to four times a day, or in sustained release form. For most large mammals, the total daily dosage is from about 100 milligrams to about 5,000 milligrams preferably from about 100 milligrams to 2,000 milligrams. Dosage forms suitable for internal use comprise from about 25 to 2,500 milligrams of the active compound in intimate admixture with a solid or liquid pharmaceutically acceptable carrier. Solid carriers include starch, lactose and kaolin, while liquid carriers include sterile water, polyethylene glycols and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants eg vitamin E, ascorbic acid, BHT and BHA.

The preferred pharmaceutical compositions from the stand-point of ease of preparation and administration are solid compositions, particularly tablets and hard-filled or liquid-filled capsules. Oral administration of Compounds I is preferred.

A representative formulation for administration orally three times a day prior to feeding in the treatment of atherosclerosis is a gelatin capsule prepared by conventional techniques to contain the following

| Ingredient | Weight (in Mg.) | | |
|---|---|---|---|
| N—(α-methylbenzyl)-cis-2-octyl-cyclopropanoctanamide | 300 | — | — |
| N—[1-(benzyl)-2-(phenyl)ethyl]-cis-2-octylcyclopropanoctanamide | — | 300 | 300 |
| corn oil | 500 | 200 | — |
| lactose | — | — | 200 |

As is the present understanding in the art, controlling the total cholesterol content of an arterial wall by inhibiting the accumulation thereof by reducing the cholesterol ester content thereof, advantageously inhibits the formation of plaques in the arterial wall.

Comparative test results are reported in Table 2 below, in which monkey aortic smooth muscle cells were originally obtained from Dr. K. Fisher-Dzoga: Univ. of Chicago, the test compound (Compound A) is N-[1-(benzyl)-2-(phenyl)ethyl]-cis-2-octylcyclopropanoctanamide.

| Compound | Protein mg/culture | Cholesterol (μg/mg cell protein) Ester | | | | Percent from control |
|---|---|---|---|---|---|---|
| | | Total | Free | Amount | mean | |
| None (Control) | 0.378 | 83.4 | 38.8 | 44.6 | | |
| | 0.442 | 75.4 | 35.4 | 40.0 | 42.0 | — |
| | 0.376 | 79.1 | 37.7 | 41.4 | | |
| A | 0.434 | 56.1 | 45.9 | 10.2 | | |
| | 0.428 | 56.9 | 45.9 | 11.0 | 10.9 | 74.0* ↓ |
| | 0.454 | 53.6 | 42.2 | 11.4 | | |

*significant at p less than 0.01

The following examples are illustrative of the invention. All temperatures are centigrade and room temperature is 20° to 30° C., unless indicated-otherwise.

Where NMR characterization data is presented, the analysis is run in CDCl$_3$ and values given in ppm; digits in parenthesis are number of protons; and b=broad, d=doublet and s=singlet.

EXAMPLE 1

(d(+))-N-(α-Methylbenzyl)-(cis)-2-Octyl-cyclopropanoctanamide

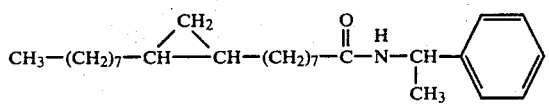

To a cooled solution of 3.0 g (cis)-2-octylcyclopropanoctanoic acid* in 70 ml methylene chloride at −20° is added first 1.0 g triethylamine and then dropwise 1.1 g ethylchloroformate. The reaction mixture is then allowed to come to room temperature and stirred for 1 hours. Then is added 1.2 g (d(+))-α-methylbenzylamine and the reaction mixture stirred for 16 hours. The reaction mixture is then extracted a few times with 2 N hydrochloric acid, then with 2 N aq. sodium hydroxide sol. and washed several times with saturated aq. sodium chloride. The organic phase is then dried over anh. sodium sulphate filtered and evaporated i.v. to dryness to obtain a residue, which upon crystallization from pentane yields the title product (m.p. 44°–46°).

*may also be called dihydrosterculic acid

EXAMPLE 2

Repeating the procedure of Example 1, but using in place of the d(+)-α-methylbenzylamine used (as a compound II) therein, an approximately equivalent amount of:
(a) 1-amino-indane;
(b) DL-tryptophan ethyl ester, hydrochloride;
(c) (d,l) α-methylenebenzylamine; (racemate);
(d) 2-methylaniline; or
(e) α-(p-methylbenzyl)-benzylamine there is accordingly obtained, respectively:
(a) N-(1-indanyl)-cis-2-octyl-cyclopropanoctanamide;
(b) α-[(1-oxo-2-octyl-cyclopropanoctylamino)]-1H-indole-3-propanoic acid, ethyl ester (cis form) as a gum, NMR: b −0.36(1), +0.6 (3); d 6.1 (1), s 8.8 (1);
(c) N-(α-methylbenzyl)-cis-2-octyl-cyclopropanoctanamide; (mixture of 2 racemates; m.p. 30°–32°);
(d) N-(o-methylphenyl)-cis-2-octyl-cyclopropanoctanamide; and
(e) N,-[α-(p-methylbenzyl)-benzyl]-cis-2-octylcyclopropanoctanamide,* m.p. 78°–81°.

*may also be called N-[1-(phenyl)-2-(p-methylphenyl)ethyl]-cis-2-octylcyclopropanoctanamide.

EXAMPLE 3

Repeating the procedure of Example 1, but using in place of the cis-2-octylcyclopropanoctanoic acid used (as a compound IV) therein, an approximately equivalent amount of:
(a) 2-hexylcyclopropanoctanoic acid;
(b) trans-2-octylcyclopropanoctanoic acid; or
(c) cis-2-tetradecylcyclopropanobutyric acid there is accordingly obtained:
(a) N-(α-methylbenzyl)-cis-2-hexyl-cyclopropanoctanamide;
(b) N-(α-methylbenzyl)-trans-2-octyl-cyclopropanoctanamide; and
(c) N-(α-methylbenzyl)-cis-2-tetradecylcyclopropanobutanamide.

EXAMPLE 4

N-[α-(p-Methylbenzyl)-p-methyl-phenylethyl]-cis-2-octyl-cyclopropanoctanamide.

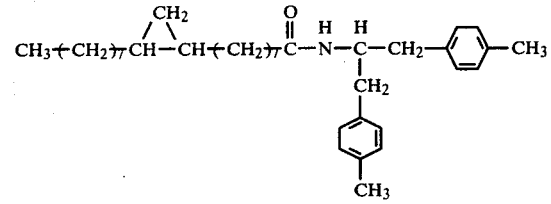

Repeating the procedure of Example 1, but using in place of the (d+) α-methylbenzylamine (as compound II) used therein, an approximately equivalent amount of α-(p-methylbenzyl)-p-methylphenylethylamine, there is accordingly obtained the title product, m.p. 60°–65°.

EXAMPLE 5

(d(+)-N-(α-Methylbenzyl-cis,cis-2-[(2-pentylcyclopropyl)-methyl]-cyclopropanoctanamide $$CH_3-(CH_2)_4-\triangle-CH_2-\triangle-(CH_2)_7-\overset{O}{\underset{\|}{C}}-N-\overset{H}{\underset{|}{C}H}-\bigcirc$$
$$\phantom{CH_3-(CH_2)_4-\triangle-CH_2-\triangle-(CH_2)_7-C-N-}CH_3$$

To a cooled solution of 3.1 g cis,cis-2-[(2-pentylcyclopropyl)-methyl]-cyclopropanoctanoic acid in 100 ml methylene chloride at −20° is added first 1.0 g triethylamine and then dropwise 1.1 g ethylchloroformate. The reaction mixture is then allowed to come to room temperature and stirred for 1 hour. Then is added 1.2 g (d(+))-α-methylbenzylamine and the reaction mixture stirred for 16 hours. The reaction mixture is then extracted a few times with 2 N hydrochloric acid, then with 2 N aq. sodium hydroxide sol. and washed several times with saturated aq. sodium chloride. The organic phase is then dried over anh. sodium sulphate filtered and evaporated i.v. to dryness to obtain the title product as an oil (mixture of diastereoisomers); NMR: b +0.7(6), −0.3(2), d 6.0(1), s 7.3(5).

EXAMPLE 6

Repeating the procedure of Example 5, but using in place of the d(+)-α-methylbenzylamine used therein (as compound II), an approximately equivalent amount of:
 (a) 1-amino-indan;
 (b) DL-tryptophan ethyl ester, hydrochloride;
 (c) (d,l)-α-methylbenzylamine; or
 (d) 2-methylaniline; respectively, there are accordingly obtained the corresponding analogous compounds I of the title product of Example 5, namely:
 (a) N-(1-indanyl)-cis,cis-2-[(2-pentylcyclopropyl)-methyl]-cyclopropanoctanamide;
 (b) α-[(1-oxo-2-pentylcyclopropyl)-methyl]-cyclopropanoctanamino)]-1H-indole-3-propanoic acid, ethyl ester (cis,cis form) as a wax: NMR: b +0.7(6), −0.3(2), d 6.2(1), s 8.5(1).
 (c) N-(α-methylbenzyl)-cis,cis-2-[(2-pentylcyclopropyl)-methyl]-cyclopropanoctanamide (mixture of diastereoisomers) as an oil, NMR0 b +0.65(6), −0.3(2), d 5.8(1), s 7.3(5); and
 (d) N-(o-methylphenyl)-cis,cis-2-[(2-pentylcyclopropyl)-methyl]-cyclopropanoctanamide.

EXAMPLE 7

1-benzyl-2-(phenyl)ethyl-(cis)-2-Octyl-cyclopropanoctanamide $$CH_3-(CH_2)_7-\overset{CH_2}{\overset{/\backslash}{CH-CH}}-(CH_2)_7-\overset{O}{\underset{\|}{C}}-N-\overset{H}{\underset{|}{C}H}\left(CH_2-\bigcirc\right)_2$$

To a cooled solution of 2.0 g (cis)-2-octylcyclopropanoctanoic acid in 70 ml methylene chloride at −20° is added first 0.707 g triethylamine and then dropwise 0.732 g ethylchloroformate. The reaction mixture is then allowed to come to room temperature and stirred for 1 hours. Then 1.5 g of 1-benzyl-2-(phenyl)ethylamine is added, and the reaction mixture stirred for 16 hours. The reaction mixture is then extracted a few times with 2 N hydrochloric acid, then with 2 N aq. sodium hydroxide sol. and washed several times with saturated aq. sodium chloride. The organic phase is then dried over anh. sodium sulphate filtered and evaporated i.v. to dryness to obtain a residue, which upon crystallization from pentane yields the title product (m.p. 40°–45°).

What is claimed is:

1. A compound of the formula:

$$A-\overset{O}{\underset{\|}{C}}-NH-\overset{COOR^4}{\underset{|}{C}H}-CH_2-\underset{\underset{R^5}{|}}{\underset{N}{\text{indole}}}-R^1$$

wherein
 A is an unsaturated fatty acid hydrocarbon chain of 7 to 23 carbon atoms in which each unsaturated ethylene moiety of the formula:

−CH=CH− is replaced by a cyclopropanyl group of the formula $$\overset{CH_2}{\overset{/\backslash}{-CH-CH-}}$$

said A having 1 to 4 such cyclopropanyl groups;
 $R^1$ is hydrogen atom, halo having an atomic weight of from about 19 to 80, alkoxy having from 1 to 3 carbon atoms; or alkyl having from 1 to 3 carbon atoms;
 $R^4$ is alkyl having from 1 to 8 carbon atoms, or unsubstituted benzyl; and
 $R^5$ is a hydrogen atom, alkyl having from 1 to 8 carbon atoms or unsubstituted benzyl.

2. A compound of claim 1 wherein A is a cyclopropanyl-bearing hydrocarbon radical of the formula:

$$CH_3\!+\!CH_2\!)_{\!n}\!-\!\!\left[\overset{CH_2}{\overset{/\backslash}{HC-\!-\!CH-CH_2\!-}}\right]_{\!m}\!\!+\!CH_2\!)_{\!p}$$

wherein n is a whole integer of from 1 to 15; m is 1 or 2; and p is a whole integer of from 1 to 13, provided that when m is 1, then n+p is from 3 to 19, 1 and when m is 2 then n+p is from 2 to 16.

3. A compound of claim 2 in which m is 1.

4. A compound of claim 2 in which the hydrogen atoms of each propanyl group are in the cis configuration.

5. A compound of claim 3 in which the total of n+p is an odd number.

6. A compound of claim 3 in which n is 7 and p is 6.

7. The compound of claim 6 which is α-[1-oxo-2-octyl cyclopropanoctylamino)]-H-indole-3-propanoic acid, ethyl (cis form).

8. A compound of claim 2 in which m is 2.

9. A compound of claim 8 in which the total of n+p is an even number.

10. A compound of claim 8 in which n is 4 and p is 6.

11. The compound of claim 10 which is α-[(1-oxo-2-pentylcyclopropyl)-methyl(cyclopropanoctanamino)]-1H-indole-3-propanoic acid, ethyl ester (cis,cis form).

* * * * *